US009063037B2

(12) United States Patent
Carrera Fabra et al.

(10) Patent No.: US 9,063,037 B2
(45) Date of Patent: Jun. 23, 2015

(54) SWAB ELUTION CHAMBER IN A TEST CARTRIDGE

(71) Applicant: STAT-DIAGNOSTICA & INNOVATION, S.L., Barcelona (ES)

(72) Inventors: Jordi Carrera Fabra, Barcelona (ES); Rafael Bru Gibert, Barcelona (ES); Anna Comengés Casas, Barcelona (ES)

(73) Assignee: STAT-Diagnostica & Innovation, S.L., Barcelona (ES)

( * ) Notice: Subject to any disclaimer, the term of this patent is extended or adjusted under 35 U.S.C. 154(b) by 39 days.

(21) Appl. No.: 13/837,160

(22) Filed: Mar. 15, 2013

(65) Prior Publication Data

US 2013/0295573 A1    Nov. 7, 2013

Related U.S. Application Data

(60) Provisional application No. 61/641,693, filed on May 2, 2012.

(51) Int. Cl.
| | | |
|---|---|---|
| *G01N 21/75* | (2006.01) | |
| *G01N 1/10* | (2006.01) | |
| *B01L 3/00* | (2006.01) | |
| *G01N 1/38* | (2006.01) | |
| *G01N 1/02* | (2006.01) | |
| *G01N 1/40* | (2006.01) | |

(52) U.S. Cl.
CPC ............... *G01N 1/10* (2013.01); *G01N 21/75* (2013.01); *B01L 3/5029* (2013.01); *G01N 1/38* (2013.01); *G01N 2001/028* (2013.01); *G01N 2001/4061* (2013.01); *B01L 3/502715* (2013.01); *B01L 2200/027* (2013.01); *B01L 2300/0809* (2013.01); *B01L 2300/1822* (2013.01); *B01L 2300/1827* (2013.01); *B01L 2400/0433* (2013.01); *B01L 2400/0481* (2013.01); *B01L 2400/0487* (2013.01)

(58) Field of Classification Search
CPC ........................................................ G01N 21/75
USPC ........................................................ 422/417
See application file for complete search history.

(56) References Cited

U.S. PATENT DOCUMENTS

| | | | |
|---|---|---|---|
| 5,884,812 A * | 3/1999 | Stawowski | 222/100 |
| 6,168,948 B1 | 1/2001 | Anderson et al. | |
| 2004/0018634 A1 | 1/2004 | Hajizadeh et al. | |
| 2006/0027686 A1 | 2/2006 | Taylor et al. | |
| 2008/0003564 A1 | 1/2008 | Chen et al. | |
| 2009/0030341 A1 | 1/2009 | Kshirsagar et al. | |
| 2010/0180980 A1 | 7/2010 | Lee et al. | |
| 2010/0274155 A1 | 10/2010 | Battrell et al. | |
| 2011/0091879 A1 | 4/2011 | Hillebrand et al. | |
| 2011/0100104 A1 | 5/2011 | Pelssers et al. | |

OTHER PUBLICATIONS

International Search Report for International Application No. PCT/EP2013/059185, European Patent Office, Netherlands, mailed on Sep. 4, 2013.

* cited by examiner

*Primary Examiner* — Ardin Marschel
(74) *Attorney, Agent, or Firm* — Sterne, Kessler, Goldstein & Fox P.L.L.C.

(57) ABSTRACT

A system and method for eluting a sample from a swab are presented. The system includes a chamber dimensioned to receive at least a portion of the length of at least one swab, a fluidic channel connected to the chamber, and an actuator. The chamber has at least one wall being a flexible film. The fluidic channel is configured to at least one of introduce and expel liquids from the chamber. The actuator is configured to contact an outer surface of the flexible film such that movement of the actuator against the outer surface of the flexible film causes a respective movement of the at least one swab when the at least one swab is disposed next to an inner surface of the flexible film. The respective movement of the at least one swab elutes the sample from the at least one swab into the chamber.

27 Claims, 4 Drawing Sheets

Figure 1:
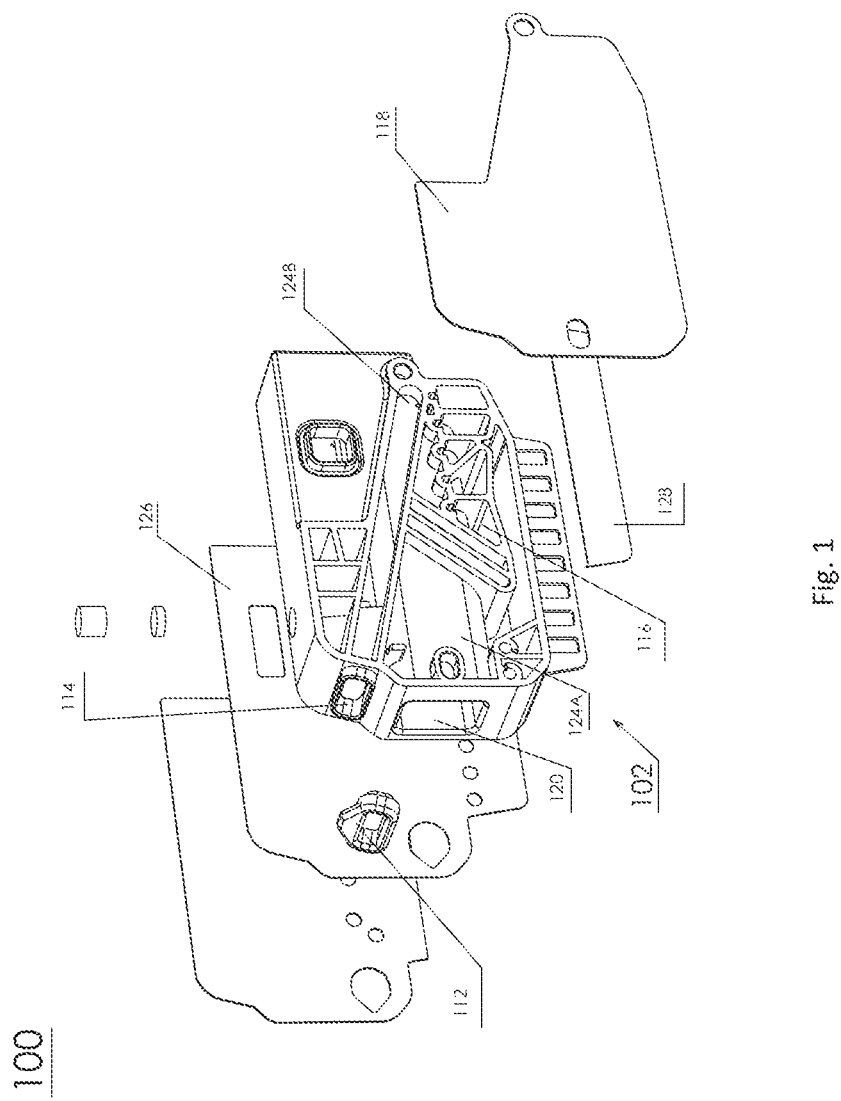

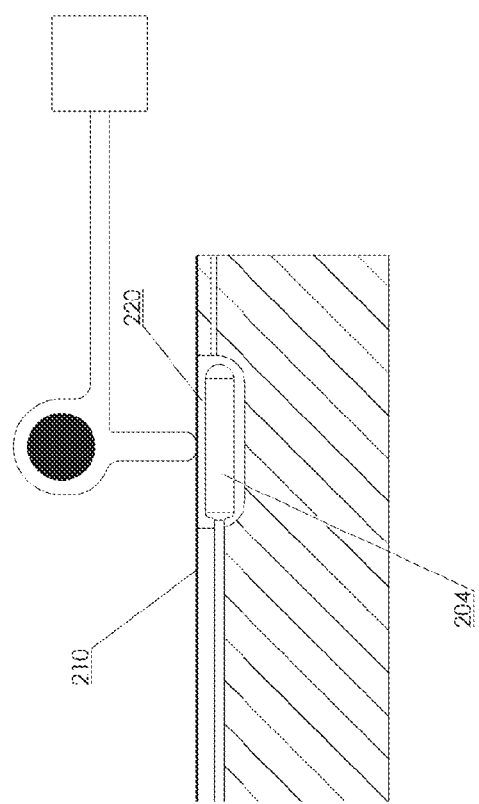
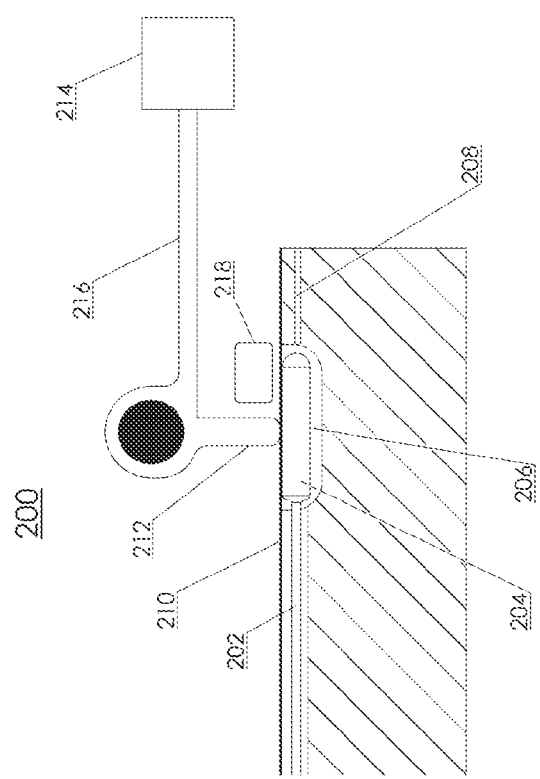

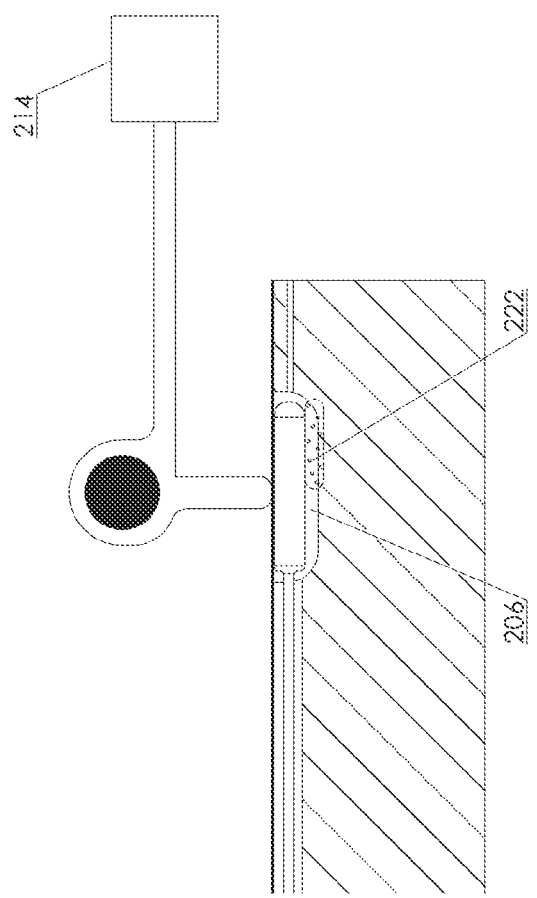

SWAB ELUTION CHAMBER IN A TEST CARTRIDGE

CROSS-REFERENCE TO RELATED APPLICATIONS

This application claims the benefit under 35 U.S.C. §119 (e), to provisional application No. 61/641,693 filed on May 2, 2012, the disclosure of which is incorporated by reference herein in its entirety.

BACKGROUND

1. Field

Embodiments of the present invention relate to the field of clinical diagnostic tools.

2. Background

Given the complexity of the automation of molecular testing and immunoassay techniques, there is a lack of products that provide adequate performances to be clinically usable in near patient testing settings. Typical molecular testing includes various processes involving the correct dosing of reagents, sample introduction, sample homogenization, lysis of cells to extract DNA and/or RNA, purification steps, and amplification for its subsequent detection. Even though there are central laboratory robotic platforms that automate these processes, for many tests requiring a short turnaround time, the central laboratory cannot provide the results in the needed time requirements.

However, it is difficult to implement systems in a clinical setting that provide accurate, trustworthy results at a reasonable expense. Given the complicated nature of various molecular testing techniques, the results are prone to error if the testing parameters are not carefully controlled or if the environmental conditions are not ideal. For example, existing instrumentation for PCR techniques has experienced high entry barriers for clinical diagnosis applications due to the background generated by exogenous sources of DNA. In the case of specific tests of pathogens, the predominant source of contamination is a result of previous reactions carried out in pipettes, tubes, or general laboratory equipment. Additionally, the use of molecular techniques for detection of microbial pathogens can produce false negatives. The false negatives may result from, for example: improper disposal of agents that inhibit the Polymerase Chain Reaction (PCR) such as hemoglobin, urine or sputum; inefficient release of DNA from cells; or low efficiency in extraction and purification of DNA and/or RNA.

The fact that molecular techniques have exceptional sensitivity levels at concentrations lower than the previous reference methods makes it rather difficult to obtain clinically relevant conclusions, while avoiding erroneous calls with false positives. To minimize this problem, especially for the detection of pathogen microorganisms, the tests must have quantification capability. It has therefore become increasingly necessary to perform multiplexed assays and vast arrays of tests to consolidate enough data to make confident conclusions. As an example, one of the main limitations of existing PCR-based tests is the inability to perform amplifications of different target genes simultaneously. While techniques such as microarrays provide very high multiplexing capacity, their main limitation is the low speed in obtaining the results, which often have no positive impact on patient management.

In order to produce relevant results from the molecular testing techniques described above, the sample to be tested must be introduced to the testing system. In many cases, samples are initially collected using cotton swabs. In this case, the sample must be eluted from the swab for further analysis. Common methods for eluting the collected sample from a swab typically involve placing the swab into a stand-alone vortexor to remove the sample. Such methods work to remove the sample, but involve performing extra steps and spending extra time during the sample preparation process. Other methods, such as simple washing, may only separate a minimal amount of sample from the swab, and may leave some of the sample on the swab.

BRIEF SUMMARY

A fluidic testing system which includes an integrated swab elution chamber is presented.

In an embodiment, a system for eluting a sample from a swab eludes a chamber dimensioned to receive at least a portion of the length of at least one swab, a fluidic channel connected to the chamber, and an actuator. The chamber has at least one wall being a flexible film having an inner surface and an outer surface. The fluidic channel is configured to at least one of introduce and expel liquids from the chamber. The actuator is configured to contact the outer surface of the flexible film such that movement of the actuator against the outer surface of the flexible film causes a respective movement of the at least one swab when the at least one swab is disposed next to the inner surface of the flexible film. The respective movement of the at least one swab elutes the sample from the at least one swab into the chamber.

In an embodiment, another system is described that includes a cartridge housing and an actuator. The cartridge housing includes a swab chamber dimensioned to receive at least a portion of the length of at least one swab, a plurality of storage chambers, a plurality of reaction chambers, and a fluidic network connecting the swab chamber, at least a portion of the plurality of storage chambers, and at least a portion of the plurality of reaction chambers to a first plurality of ports located on an inner surface of the cartridge housing. At least one wall of the swab chamber is a flexible film having an inner surface and an outer surface. The actuator is configured to contact the outer surface of the flexible film such that movement of the actuator against the outer surface of the flexible film causes a respective movement of the at least one swab when the at least one swab is disposed next to the inner surface of the flexible film.

An example method is described. The method includes positioning a swab next to an inner surface of a flexible film. The flexible film is a wall of a chamber dimensioned to receive at least a portion of the length of the swab. The method further includes flowing a liquid into the chamber via an opening. The method further includes actuating an actuator contacting an outer surface of the flexible film such that movement of the actuator on the outer surface of the flexible film causes a respective movement of the swab. The actuating elutes at least a portion of a sample from the swab into the chamber. The method further includes drawing the liquid and at least a portion of the sample from the chamber via the opening.

BRIEF DESCRIPTION OF THE DRAWINGS/FIGURES

The accompanying drawings, which are incorporated herein and form a part of the specification, illustrate embodiments of the present invention and, together with the description, further serve to explain the principles of the invention and to enable a person skilled in the pertinent art to make and use the invention.

FIG. 1 is a graphical representation of a test cartridge system, according to an embodiment.

FIGS. 2A-C display cut-away views of a swab chamber, according to an embodiment.

Figure 3:
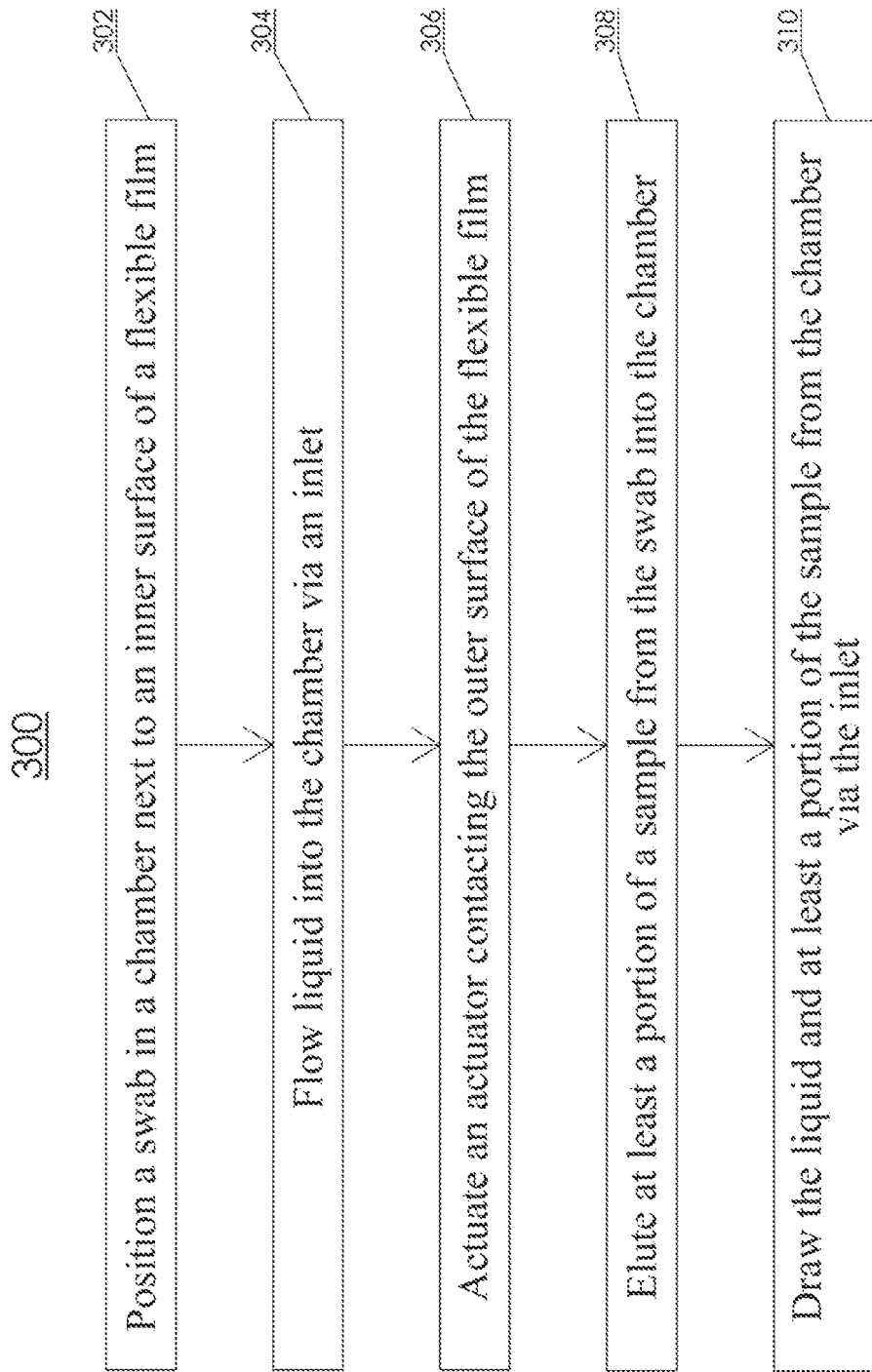

FIG. 3 illustrates a flow chart of a method, according to an embodiment.

Embodiments of the present invention will be described with reference to the accompanying drawings.

DETAILED DESCRIPTION

Although specific configurations and arrangements are discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention can also be employed in a variety of other applications.

It is noted that references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of one skilled in the art to effect such feature, structure or characteristic in connection with other embodiments whether or not explicitly described.

Embodiments described herein relate to a system and method that include an integrated swab elution chamber. The system includes a plurality of chambers connected via a fluidic network. In an embodiment, one of the plurality of chambers is a swab elution chamber configured to elute a sample from a swab placed into the swab elution chamber for further analysis.

One of the main limitations of molecular diagnostic instrumentation is the problem associated with contamination such as cross-contamination, carry-over contamination, etc. Embodiments described herein substantially eliminate by design the contamination of samples to the instrument.

In one embodiment, a test cartridge offers a self-contained liquid sealed during the manufacturing process. The sample, once introduced, does not enter into contact with the environment or with any part of the instrument. This feature of the test cartridge is also important for many laboratories and hospitals to safely dispose of the products after their use. Furthermore, the sample eluted from a swab in the swab elution chamber remains sealed within the test cartridge during an analysis cycle, according to an embodiment.

Further details relating to the components of the test cartridge system, including the swab elution chamber, are described herein with references made to the figures. It should be understood that the illustrations of each physical component are not meant to be limiting and that a person having skill in the relevant art(s) given the description herein would recognize ways to re-arrange or otherwise alter any of the components without deviating from the scope or spirit of the invention.

FIG. 1 illustrates an example test cartridge system 100 with an array of test chambers, according to an embodiment. Although reference will be made herein to the structure of example test cartridge system 100, one of skill in the art will recognize that swab elution embodiments described herein may be used with any fluidic system and configuration.

Test cartridge system 100 includes a cartridge housing 102. Other components may be considered as well for inclusion in test cartridge system 100, such as an analyzer module or various active components such as pumps or heaters.

Cartridge housing 102 includes a variety of fluidic channels, chambers, and reservoirs. For example, cartridge housing 102 may include a plurality of storage chambers 116 which may contain various buffers or other reagents to be used during an assay or PCR protocol. Cartridge housing 102 may further include one or more processing chambers 124a and 124b connected to fluidic channels along a side of cartridge housing 102. Processing chambers 124a and 124b may be used for a variety of processing and/or waste applications.

Samples are introduced into cartridge housing 102 via sample port 114, according to an embodiment. Sample port 114 may open into chamber 124b within cartridge housing 102. In one example, chamber 124b is dimensioned to completely receive the length of a common medical swab. Thus, the user may place the swab completely within sample port 114, and subsequently seal the port with a port lid 112. In another example, the swab elution chamber is dimensioned to receive a portion of the swab up to a break off point of the swab. Thus, the user may place the swab up to the break off of point through sample port 114 and then break off the remaining portion of the swab. In an embodiment, cartridge housing 102 includes more than one inlet to introduce samples.

The various chambers and channels around cartridge housing 102 may be sealed via the use of covers 118, 126, and 128. The covers may be films capable of sealing the fluid within cartridge housing 102. In another example, the covers may be plastic panels. In an example, one or more of the covers are transparent. Additionally, one or more of the covers may be thermally controlled for heating portions of housing 102.

The integrated test cartridge system 100 allows a user to place a swab sample into, for example, sample port 114, then place test cartridge system 100 into an analyzer. In embodiments, the reaction steps to be performed including, for example, purification, lysing, mixing, binding, labeling and/or detecting can all be performed within test cartridge system 100 via interaction with the analyzer without any need for the end user to intervene. Additionally, since all of the liquids remain sealed within test cartridge system 100, after the test is completed, test cartridge system 100 may be removed from the analyzer and safely disposed of without contamination of the analyzer.

FIGS. 2A-C illustrate cross section views of a system including a swab elution chamber, according to embodiments. It should be understood that the drawings are meant to illustrate only example embodiments of the invention, and that any details including relative dimensions, shapes and sizes of the various components are not meant to be limiting in any way.

FIG. 2A illustrates an example system 200 for eluting a sample from a swab, according to an embodiment. The swab has a stick 202 and a head 204. System 200 includes a swab chamber 206, an actuator 214, and a heater 218. Swab chamber 206 may be a part of cartridge housing 102. Actuator 214 may include further components such as structure 212 and lever arm 216. In an embodiment, swab chamber 206 includes a single fluidic channel 208.

The swab may be any common medical swab, such as one where head 204 is a cotton material that absorbs a sample to be tested. Head 204 may also be a plastic or foam based material. Chamber 206 may be dimensioned so as to receive only head 204 of the swab. In another example, chamber 206 is dimensioned so as to receive the entire length of the swab including the length of stick 202 attached to head 204. In yet another example, chamber 206 receives head 204 and a portion of the length of stick 202 up to a break-off point. The entrance of chamber 206 may include one or more structures to facilitate breaking stick 202 at a particular point along the length of stick 202.

In an embodiment, the entrance to chamber 206 supports the swab so that the swab is cantilevered within chamber 206. For example, chamber 206 may include one or more structures to support the swab at various points along the length of stick 202 so as to hold stick 202 in place while head 204 is free to bend.

Fluidic channel 208 may be configured to introduce and/or expel liquids from chamber 206. In an embodiment, fluidic channel 208 further connects to one or more other chambers of cartridge housing 102. For example, a negative pressure differential induced at fluidic channel 208 may draw liquid from chamber 206 into a second chamber where the sample may be mixed, lysed, reacted with another compound, etc. Liquid may be drawn into chamber 206 after introduction of the swab and before actuator 214 causes any movement to film 210. Thus, the liquid exists around at least a portion of the swab during the elution process to collect any sample eluted from the swab.

According to an embodiment, one or more walls of chamber 206 includes a film 210, such as a polymer film. Other material types may be considered as well that exhibit an elastic deformation when relatively small forces are applied. Head 204 of the swab may be positioned near film 210. In one example, head 204 of the swab is in contact with film 210. In another example, head 204 of the swab is physically separated from film 210 within chamber 206, but is still within a range of being affected by agitation of film 210. FIG. 2B illustrates an embodiment where a space 220 exists between head 204 of the swab and film 210. Film 210 is able to bend from forces applied to either side. The movement of film 210 causes head 204 of the swab to move as well, thus eluting a sample off of head 204 into chamber 206, according to an embodiment. For example, a force applied to an outer surface of film 210 causes film 210 to bend into chamber 206, thus affecting head 204 positioned near an inner surface of film 210. When head 204 of the swab is in contact with film 210, film 210 may act directly on head 204, causing head 204 to move and elute a sample off of head 204 into chamber 206. When head 204 is not in direct contact with film 210, but is still near film 210, fluid present in chamber 206 may wash around head 204. This may result in movement of head 204 and/or movement of the liquid around head 204 in such a manner as to elute a sample off of head 204 into chamber 206.

The force on the outer surface of film 210 may be applied by actuator 214. Actuator 214 may be any mechanical system that applies either a vibration or force to film 210. Actuator 214 may apply the vibration or force to an attached structure 212 that makes contact with film 210. In one example, actuator 214 includes lever arm 216 that acts to amplify any vibrations created by actuator 214. In another example, structure 212 is attached to lever arm 216 and actuator 214 induces a vibration or applies a force on lever arm 216.

Actuator 214 may apply a particular vibration frequency or range of vibration frequencies. For example, actuator 214 may apply vibrations at ultrasonic frequencies. In another example, actuator 214 applies lower frequency vibrations, such as frequencies in the range from 10 to 100 Hertz. In yet another example, actuator 214 may apply a shock vibration to the flexible film. This may be similar to striking film 210 with structure 212 producing a higher amplitude response than the frequency vibrations. In another example, actuator 214 applies a combination of frequency vibrations and shock vibrations to film 210.

The vibration or shock forces applied to film 210 may in turn cause a respective movement to head 204 of the swab. In one example, the forces are applied to head 204 due to contact between head 204 and film 210. In another example, movement of film 210 causes agitation of the liquid between head 204 and film 210. The agitated liquid causes a movement of head 204 and an eluting of a sample off of head 204 into chamber 206.

Heater 218 may be positioned at or near chamber 206. in an embodiment, heater 218 is configured to heat the contents of chamber 206. In one example, heater 218 is a Peltier device. In another example, heater 218 includes resistive heating elements. In yet another example, heater 218 is configured to blow forced air upon outer walls of chamber 206.

FIG. 2C illustrates another embodiment of a swab elution system. In an embodiment, chamber 206 includes a plurality of beads 222. The beads may be included to aid in the elution of a sample off of the swab within chamber 206. The agitation of plurality of beads 222 from the frequency vibrations or shock vibrations induced by actuator 214 works to mechanically remove the sample from the swab and elute the sample into chamber 206. Plurality of beads 222 may range in size from one micron in diameter up to 3000 microns in diameter. Additionally, plurality of beads 222 may be manufactured from various inert materials including plastics, glass, ceramics, and silica.

FIG. 3 is a flow chart illustrating an elution method 300, according to an embodiment.

At block 302, a swab is positioned in a chamber next to an inner surface of a flexible film. In an example, the flexible film may be one of the walls of the chamber. The positioning may include cantilevering the swab within the chamber so that the head of the swab is flee to bend. In one example, the swab is positioned to contact the inner surface of the flexible film. In another example, the swab is positioned near, but not touching, the inner surface of the flexible film.

At block 304, liquid flows into the chamber via an opening. The liquid may be drawn into the chamber via an applied pressure differential, according to an embodiment.

At block 306, an actuator next to the outer surface of the flexible film is actuated. The actuation causes the flexible film to move, which in turn causes a respective movement of the swab within the chamber. The actuation may include vibrating the flexible film at a given frequency, such as, for example, ultrasonic frequencies or a low frequency range between 10 and 100 Hertz. In another example, the actuation includes a shock vibration similar to striking the flexible film with a single hit and allowing the film to vibrate down on its own. In yet another example, the actuation includes a combination of frequency vibrations and shock vibrations.

At block 308, at least a portion of the sample is eluted from the swab into the chamber. The sample may mix with the liquid already present in the chamber.

At block 310, the liquid and at least a portion of the sample is drawn from the chamber via the opening. The liquid may be drawn from the chamber via an applied pressure differential, according to an embodiment. In an embodiment the liquid is drawn from the chamber and directed to another chamber around the test cartridge illustrated in FIG. 1.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The Summary and Abstract sections may set forth one or more but not all exemplary embodiments of the present invention as contemplated by the inventor(s), and thus, are not intended to limit the present invention and the appended claims in any way.

The breadth and scope of the present invention should not be limited by any of the above-described exemplary embodiments, but should be defined only in accordance with the following claims and their equivalents.

What is claimed is:

1. A system for eluting a sample from a swab comprising:
   a chamber dimensioned to receive at least a portion of the length of at least one swab, wherein at least one wall of the chamber is a flexible film having an inner surface and an outer surface;
   a fluidic channel connected to the chamber and configured to at least one of introduce and expel liquids from the chamber; and
   an actuator configured to contact the outer surface of the flexible film such that movement of the actuator against the outer surface of the flexible film causes a respective movement of the at least one swab when the at least one swab is disposed near the inner surface of the flexible film, wherein the respective movement of the at least one swab elutes the sample from the at least one swab into the chamber, and wherein the actuator is configured to induce a vibration of the flexible film at a given frequency.

2. The system of claim 1, further comprising a plurality of beads disposed within the chamber.

3. The system of claim 2, wherein the plurality of beads comprise materials selected from the group consisting of plastic, glass, ceramic, and silica.

4. The system of claim 2, wherein the plurality of beads range in diameter from 1 micron up to approximately 3000 microns.

5. The system of claim 1, wherein the chamber is configured to support the at least one swab in a cantilevered fashion next to the inner surface of the flexible film.

6. The system of claim 1, wherein the at least one swab contacts the inner surface of the flexible film.

7. The system of claim 1, wherein the actuator is configured to agitate a liquid between the inner surface of the flexible film and the at least one swab.

8. The system of claim 1, wherein the fluidic channel is further connected to one or more other chambers.

9. The system of claim 1, wherein the given frequency is an ultrasonic frequency.

10. The system of claim 1, wherein the given frequency is between 10 and 100 Hertz.

11. A system for eluting a sample from a swab comprising:
    a chamber dimensioned to receive at least a portion of the length of at least one swab, wherein at least one wall of the chamber is a flexible film having an inner surface and an outer surface;
    a fluidic channel connected to the chamber and configured to at least one of introduce and expel liquids from the chamber; and
    an actuator configured to contact the outer surface of the flexible film such that movement of the actuator against the outer surface of the flexible film causes a respective movement of the at least one swab when the at least one swab is disposed near the inner surface of the flexible film, wherein the respective movement of the at least one swab elutes the sample from the at least one swab into the chamber, and wherein the actuator is configured to induce a shock vibration to the flexible film.

12. The system of claim 11, wherein the actuator is configured to induce a combination of frequency and shock vibrations to the flexible film.

13. A system comprising:
    a cartridge housing comprising:
      a swab chamber dimensioned to receive at least a portion of the length of at least one swab, wherein at least one wall of the swab chamber is a flexible film having an inner surface and an outer surface;
      a plurality of storage chambers; and
      a fluidic network connecting the swab chamber and at least a portion of the plurality of storage chambers to a first plurality of ports located on an inner surface of the cartridge housing;
    an actuator configured to contact the outer surface of the flexible film such that movement of the actuator against the outer surface of the flexible film causes a respective movement of the at least one swab when the at least one swab is disposed near the inner surface of the flexible film; and
    a heater element configured to heat the contents of the swab chamber.

14. The system of claim 13, further comprising a plurality of beads disposed within the swab chamber.

15. The system of claim 14, wherein the plurality of beads comprise materials selected from the group consisting of plastic, glass, ceramic, and silica.

16. The system of claim 14, wherein the plurality of beads range in diameter from 1 micron up to approximately 3000 microns.

17. The system of claim 13, further comprising a lid configured to seal the swab chamber.

18. The system of claim 1, further comprising a heater element configured to heat the contents of the chamber.

19. The system of claim 11, wherein the chamber is configured to support the at least one swab in a cantilevered fashion next to the inner surface of the flexible film.

20. The system of claim 11, wherein the at least one swab contacts the inner surface of the flexible film.

21. The system of claim 11, wherein the actuator is configured to agitate a liquid between the inner surface of the flexible film and the at least one swab.

22. The system of claim 11, wherein the fluidic channel is further connected to one or more other chambers.

23. The system of claim 11, further comprising a heater element configured to heat the contents of the chamber.

24. The system of claim 11, further comprising a plurality of beads disposed within the chamber.

25. The system of claim 13, wherein the swab chamber is configured to support the at least one swab in a cantilevered fashion next to the inner surface of the flexible film.

26. The system of claim 13, wherein the actuator is configured to agitate a liquid between the inner surface of the flexible film and the at least one swab.

27. The system of claim 13, further comprising a plurality of beads disposed within the chamber.

\* \* \* \* \*